(12) United States Patent
Kim et al.

(10) Patent No.: US 9,784,677 B2
(45) Date of Patent: Oct. 10, 2017

(54) SYSTEM AND METHOD FOR REMOTELY SENSING VISIBLE RAY TRANSMITTANCE OF VEHICLE WINDOW

(71) Applicant: Electronics and Telecommunications Research Institute, Daejeon (KR)

(72) Inventors: Jong Deog Kim, Daejeon (KR); Mi-ryong Park, Sejong-si (KR); Dongseung Shin, Daegu (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 69 days.

(21) Appl. No.: 14/850,730

(22) Filed: Sep. 10, 2015

(65) Prior Publication Data

US 2016/0231243 A1 Aug. 11, 2016

(30) Foreign Application Priority Data

Feb. 6, 2015 (KR) .................. 10-2015-0018920

(51) Int. Cl.
*G01N 21/55* (2014.01)
*G01N 21/59* (2006.01)
*G01N 21/17* (2006.01)

(52) U.S. Cl.
CPC ......... *G01N 21/59* (2013.01); *G01N 21/5911* (2013.01); *G01N 2021/1793* (2013.01); *G01N 2201/06113* (2013.01); *G01N 2201/10* (2013.01)

(58) Field of Classification Search
CPC .......... G01N 2021/1793; G01N 21/59; G01N 21/5911; G01N 2201/06113; G01N 2201/10
USPC ....................................................... 356/445
See application file for complete search history.

(56) References Cited

U.S. PATENT DOCUMENTS

| | | | |
|---|---|---|---|
| 4,925,310 A * | 5/1990 | Feppon | G01N 21/59 250/341.3 |
| D362,810 S | 10/1995 | Seaburn et al. | |
| 5,546,179 A * | 8/1996 | Cheng | G01B 11/306 250/559.22 |
| 7,499,165 B2 | 3/2009 | Simpson et al. | |
| 2006/0059229 A1* | 3/2006 | Bain | G01C 21/26 709/205 |
| 2008/0154439 A1* | 6/2008 | Mira | B64D 45/0015 701/2 |
| 2010/0302528 A1 | 12/2010 | Hall et al. | |
| 2013/0010307 A1 | 1/2013 | Greiner et al. | |

(Continued)

FOREIGN PATENT DOCUMENTS

| KE | 10-2013-0140554 A | 12/2013 |
|---|---|---|
| KR | 10-2007-0115448 A | 12/2007 |

(Continued)

*Primary Examiner* — Sunghee Y Gray

(57) ABSTRACT

A vehicle window visible ray transmittance remote sensing system emits a plurality of laser beams to a driving vehicle, estimates transmittance of a window of the vehicle by acquiring a plurality of point data of a plurality of points from which a plurality of laser beams are reflected from a surface of the vehicle, and distinguishes a vehicle that deviates from a transmittance reference based on the estimated window transmittance.

19 Claims, 12 Drawing Sheets

(56) References Cited

U.S. PATENT DOCUMENTS

| | | | |
|---|---|---|---|
| 2013/0038857 A1* | 2/2013 | Funayama | G01S 17/936 356/4.07 |
| 2013/0120575 A1* | 5/2013 | Byun | H04N 7/18 348/148 |
| 2013/0235381 A1* | 9/2013 | Kroekel | B60S 1/0844 356/445 |
| 2014/0240691 A1 | 8/2014 | Mheen et al. | |
| 2015/0109603 A1 | 4/2015 | Kim et al. | |
| 2016/0187467 A1* | 6/2016 | Sato | G01S 17/10 356/5.01 |

FOREIGN PATENT DOCUMENTS

| | | | | |
|---|---|---|---|---|
| KR | 10-2015-0045735 A | | 4/2015 | |
| WO | WO2015025673 | * | 2/2015 | G01S 7/48 |

* cited by examiner

SYSTEM AND METHOD FOR REMOTELY SENSING VISIBLE RAY TRANSMITTANCE OF VEHICLE WINDOW

CROSS-REFERENCE TO RELATED APPLICATION

This application claims priority to and the benefit of Korean Patent Application No. 10-2015-0018920 filed in the Korean Intellectual Property Office on Feb. 6, 2015, the entire contents of which are incorporated herein by reference.

BACKGROUND OF THE INVENTION (a) Field of the Invention

The present invention relates to a system and method for remotely sensing visible ray transmittance of a vehicle window. More particularly, the present invention relates to a system and method for remotely sensing visible ray transmittance of a vehicle window that can provide an online traffic safety diagnosis service to a vehicle in which a detailed check is required by remotely sensing and analyzing visible ray transmittance of a window of a driving vehicle.

(b) Description of the Related Art

Tinting of a vehicle window has a merit of providing assistance in protecting skin of a human being from sunlight, enhancing air conditioning performance within the vehicle, and preventing broken glass from scattering when a car accident occurs. However, excessive blocking of visible rays by dark tinting may cause a traffic accident and may be used when committing a crime.

As a factor of a traffic accident caused by tinting of a window, an object identification ability of a driver is firstly deteriorated and a front visual field of a following vehicle is secondly blocked. Particularly, it is difficult to recognize an object at the side during the night and to secure a rear visual field through a side mirror and a rear window through tinting compared to daytime, so driving may be performed in a dangerous state.

Accordingly, most countries impose lawful regulations on injudicious tinting of the vehicle windows. For example, the Korean Road Traffic Act regulates that, when visible ray transmittance of a front surface window of a vehicle and a lateral window of a driver's seat is lower than a reference, the vehicle may interrupt traffic safety so should not be driven. Accordingly, enforcement ordinances thereof regulate that a front surface window should have visible ray transmittance of less than 70% and a lateral window of a driver's seat should have a visible ray transmittance of less than 40%.

In order to determine reference suitability of such window tinting, portable equipment that can sense transmittance and reflectivity characteristics in the entire visible ray spectrum or a 550 nm wavelength is used.

A visible ray transmittance and reflectivity measurement device presently available as a product uses a method of directly contacting a vehicle window. When measuring tinting transmittance characteristics of vehicles driving on a road with such a contact type product, much time and cost are consumed and drivers may experience great inconvenience.

Therefore, as one of systems that can detect necessary vehicle characteristics on a road when implementing a next generation traffic system such as an intelligent traffic system, a technical means that remotely senses, analyzes, and stores information on vehicles that deviate or have a high possibility of deviating from a visible ray transmittance regulation of a vehicle window of the Road Traffic Act and that provides an online traffic safety diagnosis service to a vehicle requiring a detailed check is requested.

SUMMARY OF THE INVENTION

The present invention has been made in an effort to provide a system and method for remotely sensing visible ray transmittance of a vehicle window having advantages of being capable of remotely sensing visible ray transmittance of a window of a driving vehicle and providing an online traffic safety diagnosis service to a vehicle that deviates from a visible ray transmittance reference.

An exemplary embodiment of the present invention provides a visible ray transmittance remote sensing system of a window of a driving vehicle. The visible ray transmittance remote sensing system includes a plurality of laser scanners and a signal processing controller. The plurality of laser scanners each emit a laser beam and acquire a plurality of pieces of point data of a plurality of points when the laser beam is reflected from a surface of the vehicle. The signal processing controller measures reflectivity of a window of the vehicle based on the plurality of pieces of point data and estimates reflectivity of the window based on measured reflectivity of the window.

The signal processing controller may distinguish a vehicle that deviates from a transmittance reference based on transmittance of the window.

The visible ray transmittance remote sensing system may further include a vehicle recognition unit that recognizes identification information of the vehicle, wherein the signal processing controller may store the reflectivity and the transmittance of the window to correspond to identification information of the vehicle.

The visible ray transmittance remote sensing system may further include an online information service unit that provides an online service based on the reflectivity of the window and the transmittance that is stored to correspond to identification information of the vehicle.

The plurality of laser scanners may be respectively installed in facilities that are installed on a road.

The visible ray transmittance remote sensing system may further include an environment sensor unit that detects environment information, wherein the signal processing controller may calculate a loss coefficient according to absorption and scattering of laser light in the atmosphere based on the environment information and correct reflectivity of the window based on the loss coefficient.

The environment sensor unit may include at least one detection sensor that detects at least one of a temperature, humidity, rain, an atmospheric pressure, and fine dust.

The signal processing controller may operate the system in a dormant state and a non-dormant state based on the environment information.

The plurality of laser scanners may include: a front laser scanner that acquires point data of a front window of the vehicle; a rear laser scanner that acquires point data of a rear window of the vehicle; at least one left side laser scanner that acquires point data of a left side window of the vehicle; and at least one right side laser scanner that acquires point data of a right side window of the vehicle.

The at least one left side laser scanner may be installed at different heights, and the at least one right side laser scanner may be installed at different heights.

The plurality of laser scanners may use red, green, and blue wavelength regions.

The signal processing controller may determine transmittance of the window based on a predetermined loss coefficient of the window based on reflectivity of the window and visible ray loss rate information of the window.

The signal processing controller may measure reflectivity of the window using point data of a point at which signal intensity of a laser beam is a maximum among the plurality of point data.

Another embodiment of the present invention provides a method in which a vehicle window visible ray transmittance remote sensing system senses a visible ray transmittance of a window of a driving vehicle. The method includes: emitting a plurality of laser beams; acquiring a plurality of point data of a plurality of points in which the plurality of laser beams are reflected from a surface of the vehicle; estimating reflectivity of the window based on the plurality of point data; and distinguishing a vehicle that deviates from a transmittance reference based on a transmittance of the window.

The method may further include: recognizing identification information of the vehicle; storing reflectivity and transmittance of the window that is measured from the vehicle to correspond to identification information of the vehicle; and providing an online service based on the reflectivity and the transmittance of the vehicle that is stored to correspond to identification information of the vehicle.

The estimating of reflectivity may include: measuring reflectivity of the window using point data of a point at which signal intensity of a laser beam is a maximum among the plurality of point data; and calculating transmittance based on reflectivity of a window of the vehicle.

The method may further include determining an atmosphere state based on environment information, wherein the estimating of reflectivity further includes: calculating a loss coefficient according to absorption and scattering of laser light based on the atmosphere state; and correcting the measured reflectivity using the loss coefficient.

The method may further include: determining an atmosphere state based on environment information; and controlling the vehicle window visible ray transmittance remote sensing system in a dormant state and a non-dormant state based on the atmosphere state.

The emitting of a plurality of laser beams may include: emitting a plurality of laser beams from a front laser scanner to a front window of the vehicle; emitting a plurality of laser beams from a rear laser scanner to a rear window of the vehicle; emitting a plurality of laser beams from a left side laser scanner to a left side window of the vehicle; and emitting a plurality of laser beams from a right side laser scanner to a right side window of the vehicle.

DETAILED DESCRIPTION OF THE EMBODIMENTS

Figure 1:
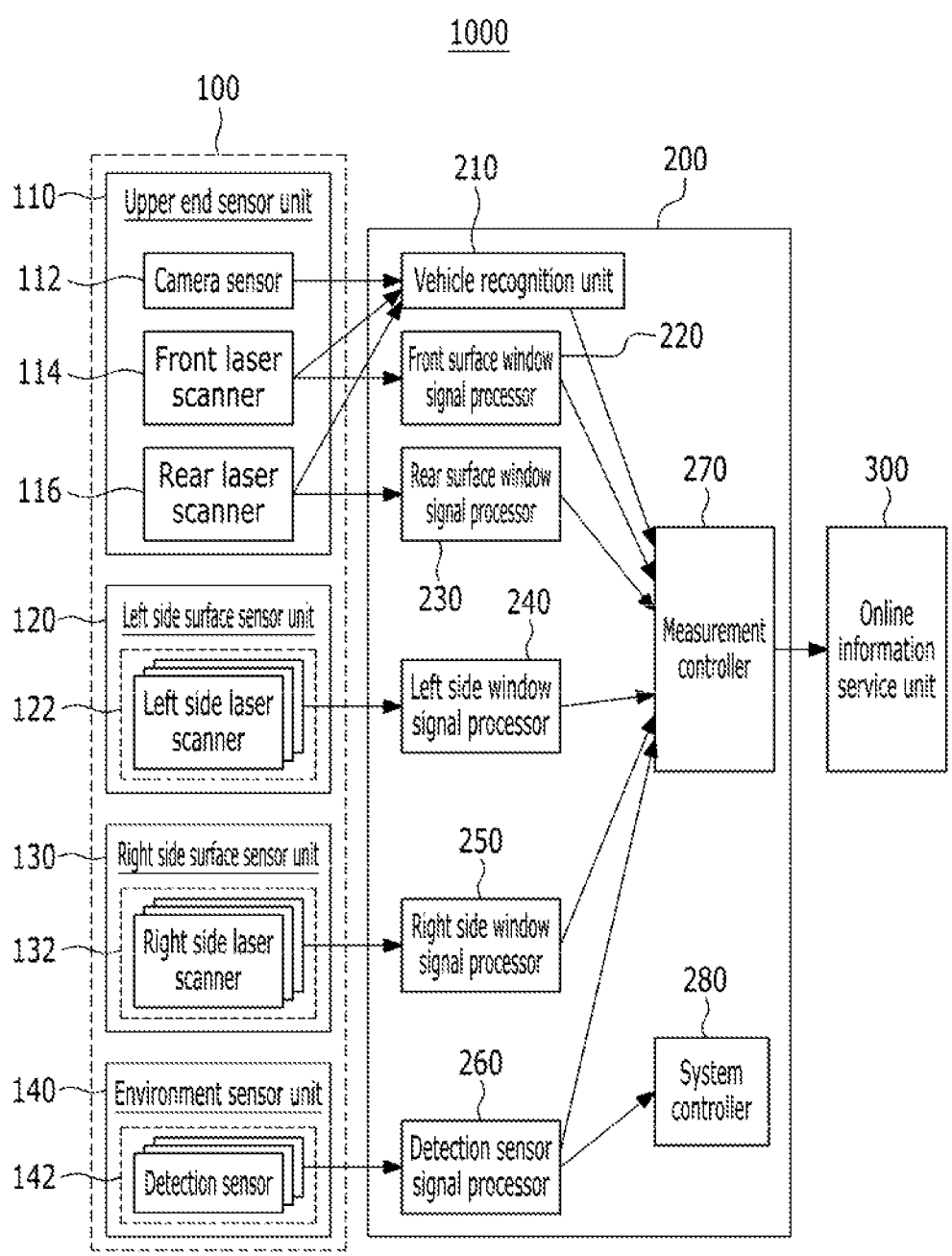
FIG. 1 is a diagram illustrating a configuration of a vehicle window visible ray transmittance remote sensing system according to an exemplary embodiment of the present invention.

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

In addition, in the entire specification and claims, unless explicitly described to the contrary, the word "comprise" and variations such as "comprises" or "comprising" will be understood to imply the inclusion of stated elements but not the exclusion of any other elements.

Hereinafter, a system and method for remotely sensing a vehicle window visible ray transmittance according to an exemplary embodiment of the present invention will be described in detail with reference to the drawings.

FIG. 1 is a diagram illustrating a configuration of a vehicle window visible ray transmittance remote sensing system according to an exemplary embodiment of the present invention.

Referring to FIG. 1, a vehicle window visible ray transmittance remote sensing system 1000 includes a sensor unit 100, a signal processing controller 200, and an online information service unit 300.

The sensor unit 100 includes an upper end sensor unit 110, a left side surface sensor unit 120, a right side surface sensor unit 130, and an environment sensor unit 140. The sensor unit 100 may be installed at a facility that is installed at, for example, an expressway tollgate or a specific point of a road.

The upper end sensor unit 110 includes a camera sensor 112 for taking an image of the vehicle, a front laser scanner 114 for sensing a front surface window of the vehicle, and a rear laser scanner 116 for sensing a rear surface window of the vehicle.

The camera sensor 112 may detect a two-dimensional image and color information of the vehicle with high resolution. The camera sensor 112 may include a stereoscopic camera. By adding location information of a relatively near object, the stereoscopic camera may form a three-dimensional image.

The left side surface sensor unit 120 includes a plurality of left side laser scanners 122 for sensing a left side surface window of the vehicle. The plurality of left side laser scanners 122 may be installed at different heights from the ground.

The right side surface sensor unit 130 includes a plurality of right side laser scanners 132 for sensing a right side surface window of the vehicle. The plurality of right side laser scanners 132 may be installed at different heights from the ground.

An eye of a normal person detects light of a visible ray region from 400 nm to 700 nm. Further, a most visible wavelength to an eye of a person is 555 nm in a green wavelength region. Therefore, the front laser scanner 114, the rear laser scanner 116, the left side laser scanner 122, and the right side laser scanner 132 have a single wavelength of about 555 nm having higher visibility than the rest of the visible ray wavelength region, but emit a laser pulse beam (hereinafter "laser beam") of a single wavelength or a plurality of wavelengths in red, green, and blue (RGB) regions, and detect a laser beam that is reflected by the vehicle to be received.

Such a front laser scanner 114, rear laser scanner 116, left side laser scanner 122, and right side laser scanner 132 emit a laser beam and acquire point data of the vehicle surface that is reflected from a surface of the vehicle. The front laser scanner 114, the rear laser scanner 116, the left side laser scanner 122, and the right side laser scanner 132 may be, for example, three-dimensional laser scanners.

The environment sensor unit 140 includes a plurality of detection sensors 142 for monitoring weather and atmosphere states. For example, a plurality of detection sensors 142 may include a temperature sensor, a humidity sensor, a raindrop sensor, an atmospheric pressure sensor, and a fine dust sensor.

The signal processing controller 200 includes a vehicle recognition unit 210, a front surface window signal processor 220, a rear surface window signal processor 230, a left side window signal processor 240, a right side window signal processor 250, a detection sensor signal processor 260, a measurement controller 270, and a system controller 280.

The vehicle recognition unit 210 basically recognizes a vehicle number, which is identification information of the vehicle, based on image information of the camera sensor 112. The vehicle recognition unit 210 additionally tracks a location and distinguishes a model (compact car/mid-sized car/full-size car, sedan/van/bus/truck) according to a time of the vehicle that is recognized based on image information of the camera sensor 112 and a detection signal of the front laser scanner 114 and the rear laser scanner 116.

The front surface window signal processor 220 recognizes a front surface window of an approaching vehicle based on point data of a laser beam that is emitted from the front laser scanner 114, calculates distance information based on a reciprocating time of a laser beam that is reflected from the front surface window, and tracks and analyzes signal intensity distribution of the reflected laser beam and distance information on a time basis, thereby measuring reflectivity of the front surface window. A function of such a front surface window signal processor 220 may be implemented in the front laser scanner 114.

The rear surface window signal processor 230 recognizes a rear surface window of a receding vehicle based on pointer data of a laser beam that is emitted from the rear laser scanner 116, calculates distance information based on a reciprocating time of a laser beam that is reflected from the rear surface window, and tracks and analyzes signal intensity distribution of the reflected laser beam and distance information on a time basis, thereby measuring reflectivity of the rear surface window. A function of such a rear surface window signal processor 230 may be implemented in the rear laser scanner 116.

The left side window signal processor 240 divides and recognizes a left side surface window of passing vehicles according to a height based on pointer data that are acquired from a plurality of left side laser scanners 122, calculates distance information based on a reciprocating time of a laser beam that is reflected from the left side surface window, and tracks and analyzes signal intensity distribution of the reflected laser beam and distance information on a time basis, thereby measuring reflectivity of the left side surface window. A function of such a left side window signal processor 240 may be implemented in the left side laser scanner 122.

The right side window signal processor 250 divides and recognizes a right side surface window of a passing vehicle according to a height based on pointer data from the plurality of right side laser scanners 132, calculates distance information based on a reciprocating time of a laser beam that is reflected from the right side surface window, and tracks and analyzes signal intensity distribution of the reflected laser beam and distance information on a time basis, thereby measuring reflectivity of the right side surface window. A function of such a right side window signal processor 250 may be implemented in the right side laser scanner 132.

The detection sensor signal processor 260 determines a sequential weather (atmosphere) state based on detection information from a plurality of detection sensors 142 of the environment sensor unit 140.

The measurement controller 270 estimates transmittance of the front surface window, the rear surface window, the left side surface window, and the right side surface window based on a reflectivity measurement result of the front surface window, the rear surface window, the left side surface window, and the right side surface window that are detected on an individual vehicle basis by the signal processing controller 200, and distinguishes an illegal vehicle that deviates from a transmittance reference of the Traffic Tax Act based on the estimated result. The measurement controller 270 stores transmittance information of the illegal vehicle.

When estimating transmittance of the front surface window, the rear surface window, the left side surface window, and the right side surface window, the measurement controller 270 may calculate loss characteristics according to absorption and scattering of laser light in the atmosphere based on an atmosphere state that is detected from the detection sensor signal processor 260, correct reflectivity by reflecting estimated loss characteristics to reflectivity that is measured by the signal processing controller 200, and estimate transmittance based on the corrected reflectivity.

The system controller 280 controls the system 1000 in a dormant state or a non-dormant state based on an atmosphere state that is detected from the detection sensor signal processor 260. The non-dormant state represents a normal operation state of the system 1000. The dormant state represents a state that operates opening and closing devices that can protect all sensors of the sensor unit 100 in a weather state in which the system 1000 cannot operate or that cannot measure within a predetermined error and in which power of all sensor units 110-130, the vehicle recognition unit 210, and the signal processors 220-250 other than the environment sensor unit 140 and the detection sensor signal processor 260 that detect a weather state is blocked.

The online information service unit 300 stores transmittance of each window and data of an illegal vehicle according to a vehicle number that is acquired from the signal processing controller 200 in an online server (not shown), and provides an online service based on stored information.

The window tinting control squad may select only an illegal vehicle within a predetermined distance from a remote measurement location for a vehicle window transmittance check based on information that is stored by the online information service unit 300, and performs a thorough check of the selected illegal vehicle using a portable measurement device, and thus disturbance of traffic flow due to traffic enforcement and manpower and time that are consumed for traffic enforcement can be minimized. Further, the control squad may impose a fine to an illegal vehicle as a thorough check result, and an illegal vehicle driver may receive package guidance on determination of a measurement checkup and thorough checkup result, fine payment, and a re-checkup procedure after improvement measurement on line.

Figure 2:
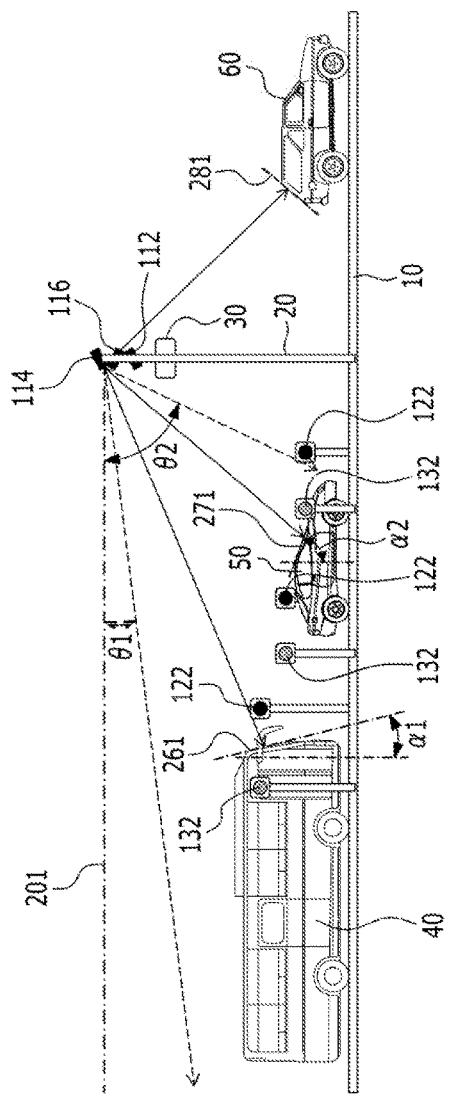
FIG. 2 is a layout view illustrating an example in which a sensor unit of FIG. 1 is installed in a facility on a road when viewed from a side surface of a vehicle.

FIG. 2 is a layout view illustrating an example in which a sensor unit of FIG. 1 is installed in a facility on a road when viewed from a side surface of a vehicle, and in FIG. 2, the signal processing controller 200 and the online information service unit 300 are omitted. As shown in FIG. 2, the camera sensor 112 of the upper end sensor unit 110, the front laser scanner 114, and the rear laser scanner 116 may be installed in an upper end portion of the facility 20 on a road, may be installed at different vertical heights from the ground 10, or may be installed at the same vertical height at different horizontal locations from the ground 10.

The front laser scanner 114 scans between a minimum angle θ1 and a maximum angle θ2 in a left side-lower direction of a horizontal surface 201, thereby acquiring point data of each reflection point.

When a surface 261 of the front surface window has a relatively small angle α1 with respect to a horizontal direction, as with a bus 40, an advancing direction of a laser beam of the front laser scanner 114 and the surface 261 of the front surface window become perpendicular at a relatively far distance and thus signal intensity of a laser beam that is reflected to the front laser scanner 114 becomes a maximum.

When a surface 271 of the front surface window has a relatively large angle α2 with respect to a horizontal direction, as with a passenger car 50, an advancing direction of a laser beam of the front laser scanner 114 and the surface 271 of the front surface window become perpendicular at a relatively near distance and thus signal intensity of a laser beam that is reflected to the front laser scanner 114 becomes a maximum.

Therefore, among point data that are acquired at the front laser scanner 114, reflectivity of a front surface window and a distance at a point thereof are measured by the front surface window signal processor 220 from point data in which signal intensity is a maximum.

Similarly, the rear laser scanner 116 acquires point data of a laser beam that is reflected from a surface 281 of a rear surface window of a receding vehicle 60, and reflectivity of a rear surface window and a distance at a point thereof are measured by the rear surface window signal processor 230 from point data in which signal intensity is a maximum among acquired point data.

A plurality of left side laser scanners 122 of the left side surface sensor unit 120 of FIG. 1 are installed at facilities, respectively, that are located at the left side of a driving road of FIG. 2, and a plurality of right side laser scanners 132 of the right side surface sensor unit 130 of FIG. 1 are installed at facilities, respectively, that are located at the right side of a driving road of FIG. 2. In FIG. 2, three left side laser scanners 122 and three right side laser scanners 132 are illustrated. In this case, when various models of vehicles pass through a scanning area, a quantity, a gap, and an angle of the laser scanners 122 and 132 may be determined to measure to correspond to a window height thereof.

The left side laser scanners 122 and the right side laser scanners 132 acquire point data with the same method as that of the front laser scanner 114.

The plurality of left side laser scanners 122 are installed at different heights from the ground 10. Particularly, the plurality of left side laser scanners 122 may be installed so that a height of the left side laser scanner 122 rises while advancing from the near side to the far side from the front laser scanner 114. Thereby, by enabling a measurement time interval of a front surface window and a side surface window of the same vehicle to be more adjacent, time synchronization of measurement data may be more easily performed.

The plurality of right side laser scanners 132 may be installed similar to the plurality of left side laser scanners 122. That is, the plurality of right side laser scanners 132 are installed at different heights from the ground 10. Particularly, a plurality of right side laser scanners 132 may be installed so that a height of the right side laser scanner 132 rises while advancing from the near side to the far side of the front laser scanner 114.

As a detailed example, as described above, in a general bus 40, because a slope of a front surface window is small, at a relatively far distance from the front laser scanner 114, reflectivity can be accurately measured and thus a location of the left/right side laser scanner 122/132 having a high height may be determined to correspond to a periphery of a reflectivity measurement distance.

In contrast, in a passenger car 50 in which a slope of a front surface window is large, at a relatively near location from the front laser scanner 114, because reflectivity can be accurately measured, it may be effective to dispose the left/right side laser scanner 122/132 having a low height at a near location from the front laser scanner 114.

Further, when using laser scanners of the same wavelength, because mutual interference may occur between the left/right side or vertical left/right side laser scanners 122/132, the plurality of left/right side laser scanners 122/132 may be alternately installed at the road side, as shown in FIG. 2.

When wavelengths of the facing left side laser scanner 122 and right side laser scanner 132 are different or when the left/right side laser scanner 122/132 having a scanning distance smaller than a lane width and having a noise filtering function is used, a plurality of left/right side laser scanners 122/132 may be installed at the same facing location and may be installed at different heights according to a vehicle.

The plurality of detection sensors 142 of the environment sensor unit 140 are integrated to be produced in one sensor module 30, and the sensor module 30 may be installed in the facility 20. Alternatively, each detection sensor 142 may be distributed and installed in facilities for the system 1000 to correspond to a detection function.

Figure 3:
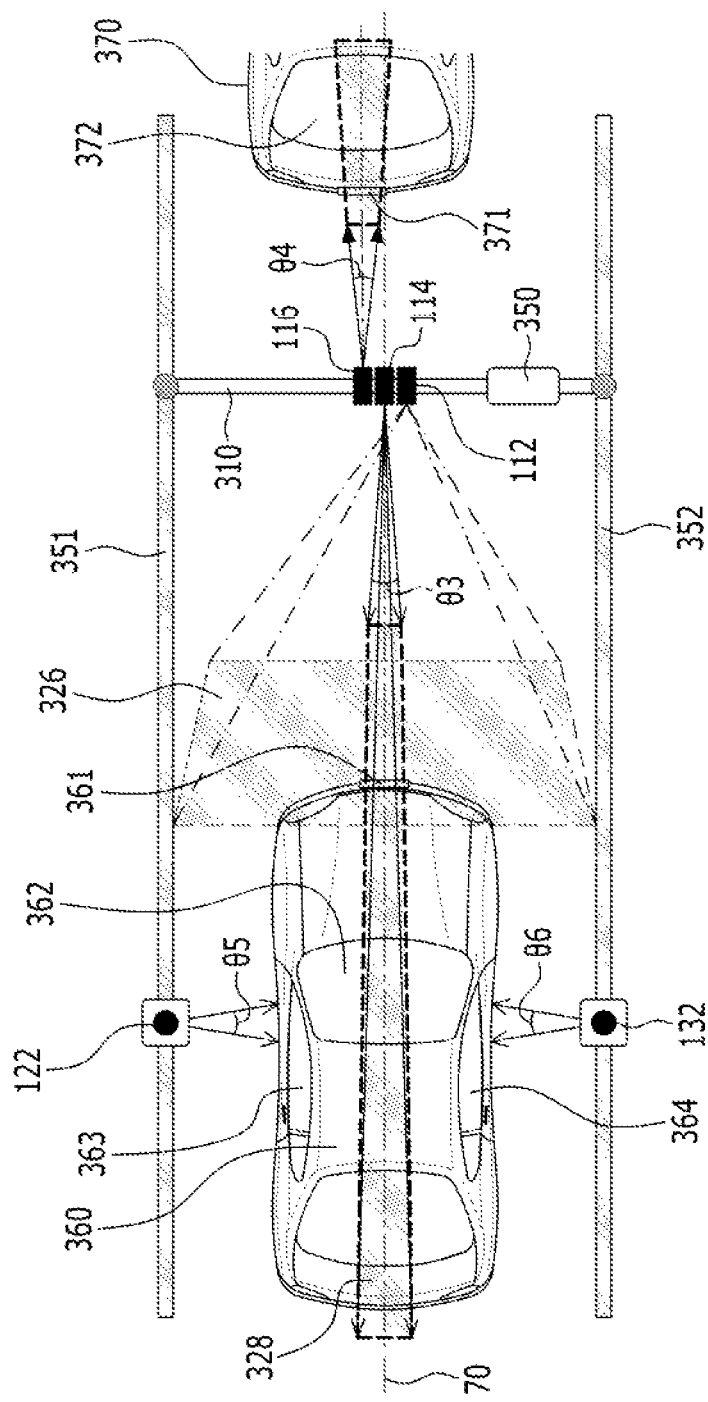
FIG. 3 is a layout view illustrating an example in which a sensor unit of FIG. 1 is installed in a facility on a road when viewed from the top of a vehicle driving on the road.

FIG. 3 is a layout view illustrating an example in which a sensor unit of FIG. 1 is installed in a facility on a road when viewed from the top of a vehicle driving on the road.

Referring to FIG. 3, at an upper end portion of a facility 310 that is installed by standing an iron pole at peripheries 351 and 352 of a road, the camera sensor 112, the front laser scanner 114, and the rear laser scanner 116 may be installed. FIG. 3 illustrates that the camera sensor 112, the front laser scanner 114, and the rear laser scanner 116 are installed at different horizontal locations and the same vertical location.

At facilities that are installed at the peripheries 351 and 352, respectively, of a road, the left/right side laser scanner 122/132 may be installed. In this case, unlike a case of FIG. 2, at the peripheries 351 and 352 of the road, a left/right side laser scanner 122/132 may be installed. In this way, when a left/right side laser scanner 122/132 is installed at the peripheries 351 and 352 of the road, it is appropriate for a case in which an exclusive lane is set to correspond to a specific model of a compact car, a mid-sized car, and a full-size car, and in this case, an installation location of the left/right side laser scanner 122/132 may be determined according to a corresponding model.

The camera sensor 112 is installed to have a predetermined angle toward the front ground at an upper end portion of the facility 310, and an image area 326 that is projected to the ground on a road by the camera sensor 112 has a form of FIG. 3 when viewed from the top. Therefore, as shown in FIG. 3, when the vehicle 360 enters the image area 326, the camera sensor 112 acquires a two-dimensional image including a vehicle license plate 361 of the vehicle 360.

As described with reference to FIG. 2, the front laser scanner 114 pointer scans a predetermined angle range θ3 in a lateral direction of a horizontal axis 70 while point scanning a predetermined angle range in a vertical direction. Therefore, an area 328 of laser points that are radiated to the ground on a road may have a form similar to that of FIG. 3 when viewed from the top. The front laser scanner 114 radiates a laser beam and receives a laser beam that is reflected by the vehicle 360, and as shown in FIG. 3, when the vehicle 360 is located in the area 328, a received signal includes three-dimensional information about an intermediate portion of the front surface license plate 361, a hood, a front surface window 362, and a top when viewed from a front surface of the vehicle 360 together with information about the ground. Therefore, the front laser scanner 114 recognizes a form of the vehicle 360 from three-dimensional information of received signals, thereby recognizing an area of the front surface window.

Further, a portion of a laser beam that is radiated from the front laser scanner 114 to the window is reflected or scattered to be primarily received by the front laser scanner 114 and another portion thereof is transmitted to be reflected by objects within the vehicle 360 and to be thus secondarily received by the front laser scanner 114, and when using such a characteristic of a received signal together, the front laser scanner 114 may more accurately distinguish data of the front surface window 362.

The rear laser scanner 116 pointer scans in a predetermined angle range in a vertical direction together with a predetermined angle range θ4 in a horizontal direction with the same method as that of the front laser scanner. Therefore, a signal that is received by the rear laser scanner 116 includes three-dimensional information about a portion of a rear surface license plate 371 of a vehicle 370, a trunk, a rear surface window 372, and a top together with information about the ground. Therefore, the rear laser scanner 116 may recognize a form of the vehicle 370 from three-dimensional information of received signals and thus may recognize an area of the rear surface window.

The left side laser scanner 122 and the right side laser scanner 132 perform pointer scanning with a predetermined angle range in a vertical direction together with predetermined angle ranges θ5 and θ6 in a horizontal direction of the left side surface window 363 and a right side surface window 364 of the vehicle 360, thereby collecting three-dimensional information of a side surface of the vehicle 360 with the foregoing method.

Further, the front laser scanner 114, the rear laser scanner 116, the left side laser scanner 122, and the right side laser scanner 132 generate one piece of three-dimensional frame information using three-dimensional information that is collected for a predetermined time interval and continuously generate next frame information. Therefore, as the vehicle 360 moves, reflectivity of a corresponding window may be measured at the front side and reflectivity of a corresponding window may be measured at the rear side.

As described with reference to FIG. 2, a plurality of detection sensors 142 of the environment sensor unit 140 may be integrated to be produced in a sensor module 350, and the sensor module 350 may be installed in the facility 310.

Figure 4:
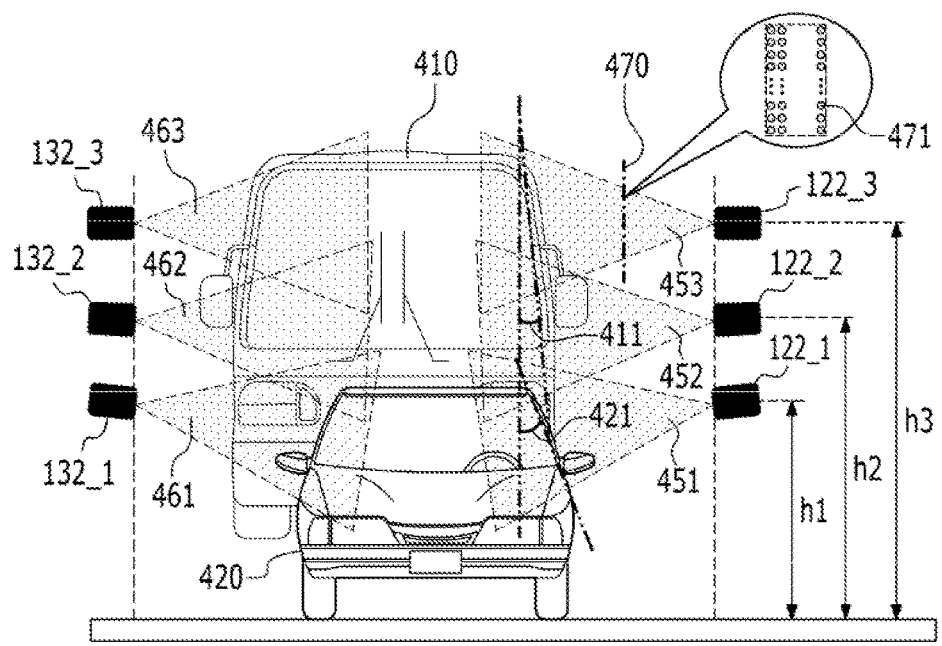
FIG. 4 is a layout view illustrating an installation example of laser scanners of a left side surface sensor unit and a right side surface sensor unit when viewed from the front of a driving vehicle according to an exemplary embodiment of the present invention.

FIG. 4 is a layout view illustrating an installation example of a left laser scanner and a right laser when viewed from the front of a driving vehicle scanner according to an exemplary embodiment of the present invention.

Referring to FIG. 4, a plurality of left side laser scanners 122_1, 122_2, and 122_3 are installed to have different heights h1-h3 to correspond to a height of a small size vehicle, a mid-size vehicle, and a large size vehicle. A plurality of right side laser scanners 132_1, 132_2, and 132_3 are also installed to have different heights h1-h3.

Further, the left side laser scanners 122_1, 122_2, and 122_3 and the right side laser scanners 132_1, 132_2, and 132_3 may be installed so that a portion of vertical angle ranges 451-453 and 461-463 of a laser point has a predetermined slope to a horizontal direction to correspond to a characteristic and an installation condition of a window according to a model to measure. The laser point represents a portion that is hit by a laser beam. Here, a characteristic of a window according to a model represents that a slope 421 of a side surface window of a small size vehicle such as the passenger car 420 to a vertical direction is larger than a slope 411 of a large size vehicle such as a bus 410. Further, an installation condition may include a minimum height. For example, because the left/right side laser scanner 122_1/132_1 that is installed at a low location may be polluted by a cloud of dust and rainwater of the road side, the left/right side laser scanner 122_1/132_1 may be set at a higher height than a minimum height.

As described above, a distribution of a laser point that is emitted from the left side laser scanners 122_1, 122_2, and 122_3 and the right side laser scanners 132_1, 132_2, and 132_3 has a constant angle range in both a vertical direction and a horizontal direction.

For example, a cluster distribution 471 of a laser point for a cross-section of a direction of a vertical axis 470 may be represented, as shown in FIG. 4, and lines of the laser point are formed to repeat in parallel in a vertical direction and a lateral direction. In another exemplary embodiment, lines of a laser point may be formed to have a lateral distribution in a zigzag form while vertically advancing.

Figure 5:
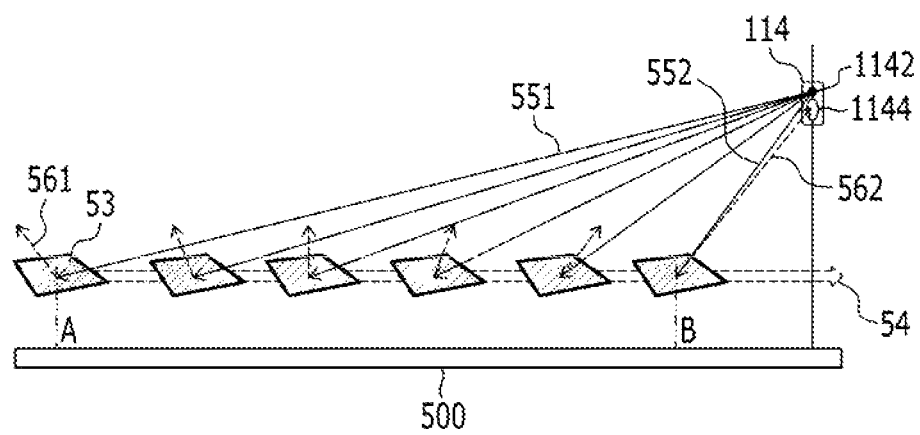
FIG. 5 is a diagram illustrating maximum reflection characteristics of a laser beam of a front laser scanner according to a driving direction movement of a front surface window.

FIG. 5 is a diagram illustrating maximum reflection characteristics of a laser beam of a front laser scanner according to a driving direction movement of a front surface window.

Referring to FIG. 5, the front laser scanner 114 includes a transmitting unit 1142 and a receiving unit 1144. A front surface window 53 of the vehicle moves in a driving direction 54 from a location A to a location B at a constant height from the ground 500.

As in the cluster distribution 471 of a laser point of FIG. 4, the transmitting unit 1142 of the front laser scanner 114 performs scanning with a predetermined point gap in a horizontal angle range and a vertical angle range. The receiving unit 1144 of the front laser scanner 114 acquires point data from a signal that is reflected by the vehicle.

For example, the transmitting unit 1142 may perform scanning with a point gap of an angle 0.1° in a range of 5° horizontal×60° vertical, and for this reason, the transmitting unit 1142 emits laser points in respective intrinsic angles, such as 50×600 points in the horizontal and vertical direction, respectively.

Accordingly, point data that are collected in the receiving unit 1144 of the front laser scanner 114 include information of about 30,000 intrinsic angles and is referred to as single three-dimensional frame data. That is, single three-dimensional frame data is three-dimensional information data that is collected from the receiving unit 1144 of the front laser scanner 114 by scanning one time a horizontal×vertical angle that laser beams of the front laser scanner 114 target. For reference, a translucent object may generate several return pulses by a single laser beam in each intrinsic angle, and when it is assumed that the receiving unit 1144 of the front laser scanner 114 collects a maximum of three return pulse peaks, the receiving unit 1144 may collect a maximum of three pieces of point data from each piece of intrinsic angle information.

Because a consumed time when laser light reciprocates over a distance of 35 m at the speed of light is about 0.23 µs, a consumed time when the front laser scanner 114 collects single three-dimensional frame data including 30,000 intrinsic angles becomes 7/1000 second with simple calculation without a time such as for signal processing. When the vehicle drives at a speed of 60 km/h for this time, the vehicle moves about 0.117 m.

In FIG. 5, when the front surface window 53 having a relatively large slope in a vertical direction is located at a periphery of a location A, it is assumed that three-dimensional frame data is received in the receiving unit 1144 of the front laser scanner 114. In this case, in three-dimensional frame data, i.e., receiving frame data that is reflected and scattered from a surface of the front surface window 53 to be received by the receiving unit 1144, when it is assumed that a specific laser point has maximum reception intensity at an intrinsic angle of a laser beam 551 from the transmitting unit 1142, an actually reflected laser beam 561 does not advance toward the receiving unit 1144 and thus in this case, maximum reception intensity is weak.

However, as shown in FIG. 5, as the front surface window 53 approaches the front laser scanner 114, an intrinsic angle of a laser beam representing maximum reception intensity in each piece of three-dimensional frame data is changed, and when a location of the front surface window 53 finally arrives at a location B, a reflected beam 562 of a laser beam 552 is directly applied to the receiving unit 1144 to represent maximum reception intensity.

The front laser scanner 114 according to an exemplary embodiment of the present invention continuously scans a predetermined angle range, collects continuous three-dimensional frame data from a window of a moving vehicle by an emitted laser beam, and measures reflectivity based on maximum reception intensity when a laser beam that is directly reflected from the window is directly applied to the receiving unit 1144.

Figure 6:
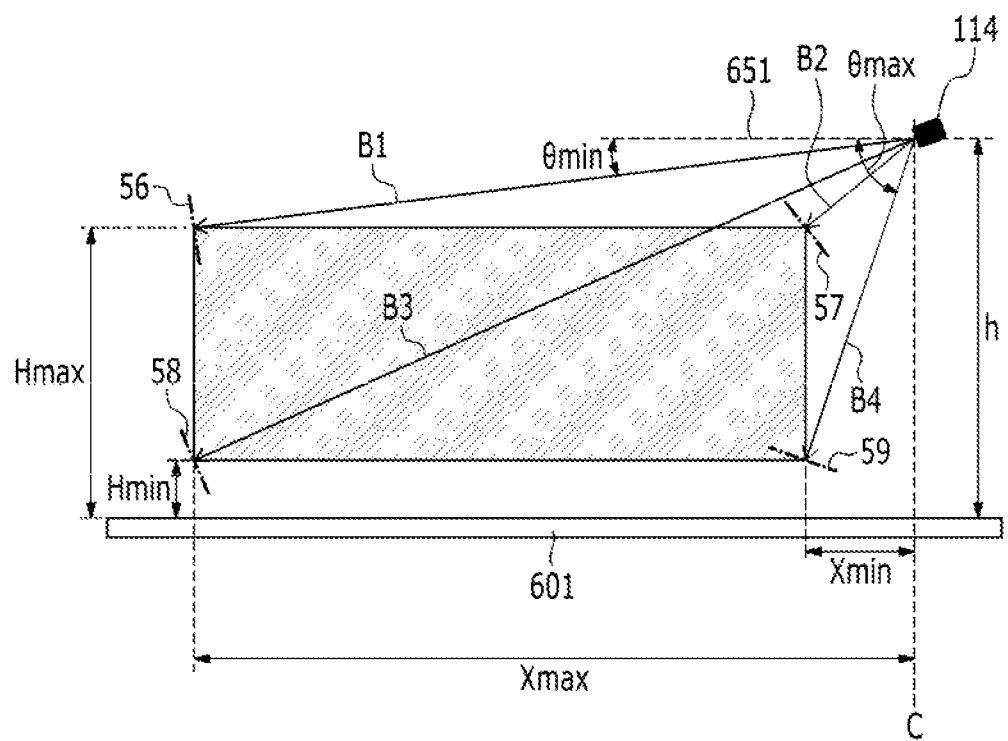
FIG. 6 is a diagram illustrating a relationship of a scanning vertical angle range, a measurement height, and a measurement distance of a front laser scanner according to an exemplary embodiment of the present invention.

FIG. 6 is a diagram illustrating a relationship of a scanning vertical angle range, a measurement height, and a measurement distance of a front laser scanner according to an exemplary embodiment of the present invention.

As shown in FIG. 6, the front laser scanner 114 is installed at a height h. For all vehicles existing within a distance range between Xmin and Xmax from a location C of the front laser scanner 114, when a height of a front surface window is a minimum of Hmin to a maximum of Hmax from the ground 601, a scanning angle of the front laser scanner 114 should be a minimum of θmin to a maximum of θmax to a horizontal axis 651.

Slopes 56-59 of a window that can measure according to a height of the front surface window are shown in FIG. 6. That is, when it is assumed that a vehicle is located between Xmin and Xmax, if a height of the front surface window is Hmax, a slope of the window that can be measured has a value between a slope 56 and a slope 57. Similarly, when a window height is Hmin, a slope of the window that can be measured has a value between a slope 58 and a slope 59. FIG. 6 illustrates that laser beams B1-B4 are perpendicular to the window slopes 56, 57, 58, and 59, respectively.

As shown in FIG. 5, the transmitting unit 1142 and the receiving unit 1144 of the front laser scanner 114 generally have a predetermined gap, but when the predetermined gap has a very small value that can be disregarded, compared with a measuring distance, the transmitting unit 1142 and the receiving unit 1144 may be simplified in a corresponding form, as shown in FIG. 6.

A distance of a window that the front laser scanner 114 can measure may be represented by Equation 1.

$$X = [h(\text{top}) - H] * \cot(\alpha) \qquad \text{(Equation 1)}$$

In Equation 1, h(top) represents a height h of the front laser scanner 114, H and X represent a height and a distance of a window, respectively, and α represents a slope angle of a window to a vertical direction.

The rear laser scanner 116 may be installed at a height that is determined based on Equation 1.

Figure 7:
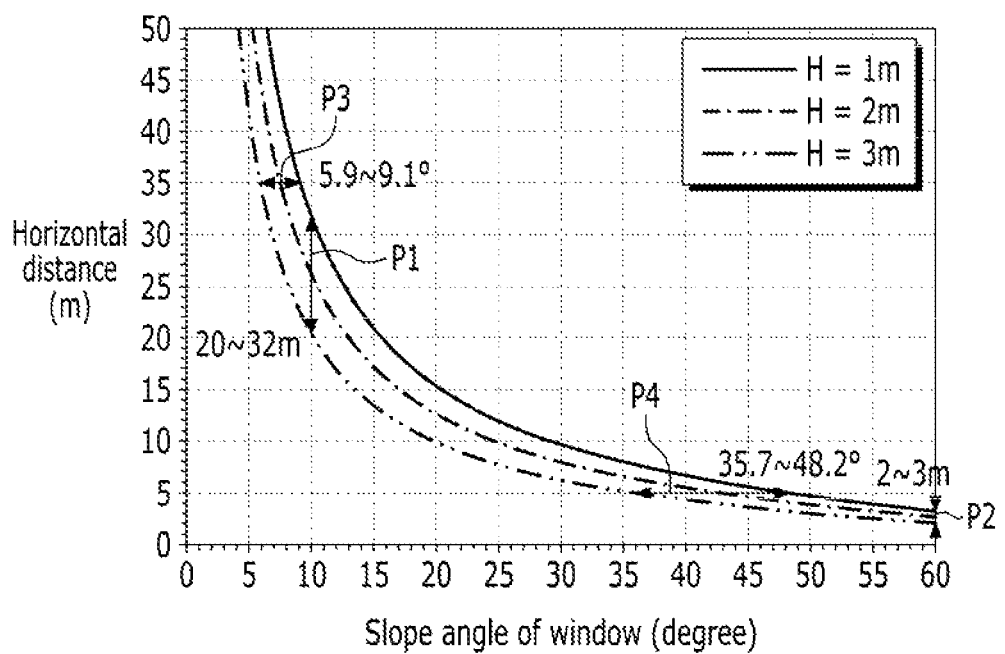
FIG. 7 is a graph illustrating a relationship of a measurement distance of a horizontal direction to a slope angle of a front surface window.

FIG. 7 is a graph illustrating a relationship of a measurement distance of a horizontal direction to a slope angle of a front surface window, and illustrates a relationship of a measurement distance of a horizontal direction to a slope angle of a front surface window when h(top) is 6.6 m and H is 1 m, 2 m, and 3 m in Equation 1.

As shown in FIG. 7, when it is assumed that various models of vehicles have a front surface window having a slope angle of 10° and that a height H thereof has a value of 1-3 m, when the vehicle is located at a horizontal distance of about 20-32 m (P1) from the front laser scanner 114, the front laser scanner 114 can measure.

Further, when it is assumed that a slope of the front surface window is 60° and that a height H of the front surface window has a value of 1-3 m, a horizontal distance that can be measured by the front laser scanner 114 is calculated as about 2-3 m (P2). From another viewpoint, in a vehicle that is located at a 35 m point, a slope angle of a front surface window that the front laser scanner 114 can measure becomes a value P3 of about 5.9°-9.1° according to a height (H=1-3 m) of the window. In a vehicle that is located at a 5 m point, a slope angle of a window that is measured according to a height (H=1-3 m) of the front surface window becomes a value P4 of about 35.7°-48.2°.

Figure 8:
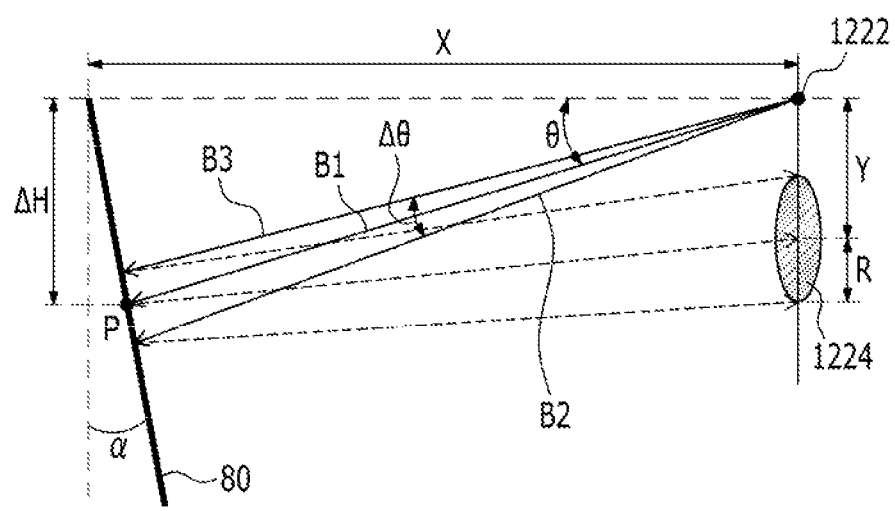
FIG. 8 is a diagram illustrating a correlation between transmitting/receiving laser beams to a window slope of a left side laser scanner according to an exemplary embodiment of the present invention.

FIG. 8 is a diagram illustrating a correlation between transmitting/receiving laser beams to a window slope of a left side laser scanner according to an exemplary embodiment of the present invention. FIG. 8 illustrates the left side laser scanner 122, but the same content may be applied to the right side laser scanner 132.

As shown in FIG. 8, the left side laser scanner 122 includes a transmitting unit 1222 and a receiving unit 1224, as in the front laser scanner 114.

It is assumed that a center gap of the transmitting unit 1222 and the receiving unit 1224 is Y and a radius of a light receiving area of the receiving unit 1224 is R. When a laser beam from the transmitting unit 1222 is reflected to a window 80 to enter the center of a light receiving area of the receiving unit 1224, an angle between a transmitting laser beam B1 thereof and a horizontal axis is represented by θ, and an angle between laser beams B2 and B3 that are reflected to an edge of a light receiving area of the receiving unit 1224 to enter is represented by Δθ.

In FIG. 8, when a straight line distance between the transmitting unit 1222 and a laser point P is represented by L and a vertical distance between a horizontal axis passing through the transmitting unit 1222 and a laser point P is represented by ΔH, a correlation of a slope angle α of a window and a center gap of the transmitting unit 1222 and the receiving unit 1224 to Y may be represented by Equation 2.

$$\Delta H \approx L * SIN\ [(Y/2L)*(180/\pi)+\alpha] \qquad \text{(Equation 2)}$$

Further, in FIG. 8, a relationship of Δθ, L, and R may be approximated, as in Equation 3.

$$\Delta\theta \approx R/L \qquad \text{(Equation 3)}$$

A relationship of Equations 2 and 3 may be applied when a measurement distance is not very large, compared with a center gap between the transmitting unit 1222 and the receiving unit 1224 like the left side or right side laser scanners 122 and 132.

Figure 9:
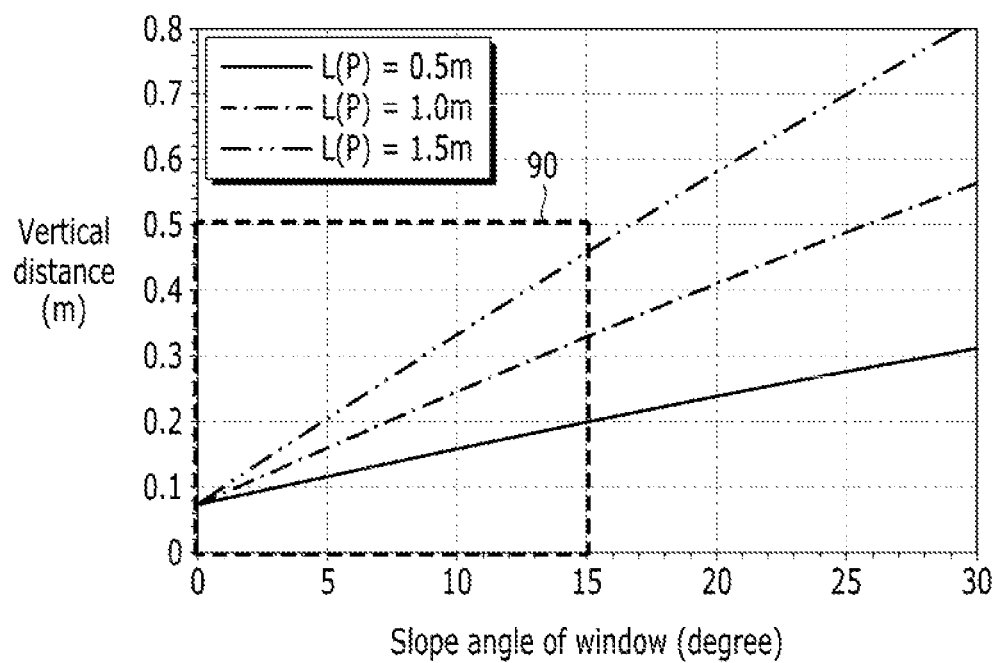
FIG. 9 is a graph illustrating a correlation between a slope angle and a vertical distance of a window when a center gap of a transmitting unit and a receiving unit of a left side laser scanner is 0.15 m according to an exemplary embodiment of the present invention.

FIG. 9 is a graph illustrating a correlation between a slope angle and a vertical distance of a window when a center gap of a transmitting unit and a receiving unit of a left side laser scanner is 0.15 m according to an exemplary embodiment of the present invention.

As shown in FIG. 9, in a graph when respective measurement distances [L(P)] from the transmitting unit 1222 of the laser scanner 122 are 0.5 m, 1.0 m, and 1.5 m, if a slope angle of the left side surface window is 0-15°, a vertical distance deviation of a point P where reflectivity can be measured becomes within 0.4 m. In consideration of such a characteristic, in order to measure a vehicle of various models according to a size and a height of the left side surface window, a quantity, a height, and a gap of the left side laser scanner 122 that should be disposed at a left side surface of a road may be determined. For the right side laser scanner 132, a quantity, a height, and a gap may be determined with the same method.

For example, a minimum width of a road having a speed limit of less than 60 km/h is 3 m, and in an expressway having a speed limit of 80 km/h or more, because a minimum width is 3.50 m, a distance for measuring reflectivity of the left side surface window from the left side laser scanner 122 may be set to a range of 0.5-1.5 m.

Therefore, when a vertical direction minimum size of the left side surface window is 0.4 m or more and when a slope angle is 0-15°, a gap of a disposition height of the left side laser scanner 122 should be within 0.4 m, and thus in order to measure a window of a height of 1-3 m from the ground, at the left side surface, a minimum of four laser scanners may be disposed.

In Equation 3, when R is 0.05 m, at a distance of about 0.5-1.5 m, Δθ has an angle of about 5.7-1.9°. Therefore, when an angle between neighboring laser beams that are emitted from the transmitting unit 1222 of the left side laser scanner 122 is 0.1°, a plurality of maximum reflected beams are applied to a light receiving area of the receiving unit 1224. In this way, point data of a receiving angle that may have a plurality of maximum reflection intensities is effective in measuring more accurate reflectivity even in various conditions that can occur by a change, a vibration, and window contamination according to a movement of the vehicle.

Figure 10:
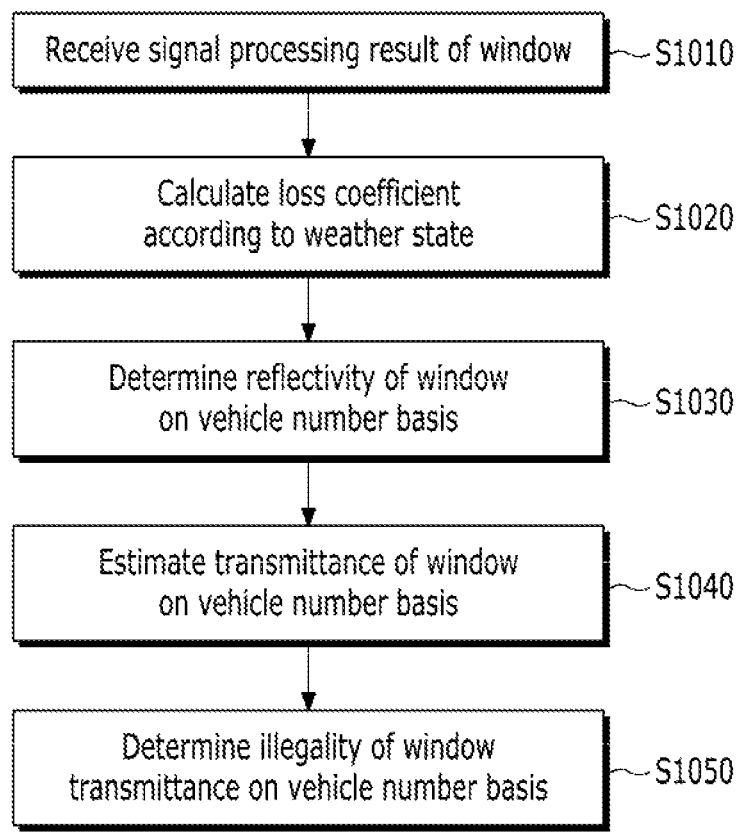
FIG. 10 is a flowchart illustrating a method of estimating window transmittance according to a vehicle number in a measurement controller of FIG. 1.

FIG. 10 is a flowchart illustrating a method of estimating window transmittance according to a vehicle number in a measurement controller of FIG. 1.

Referring to FIG. 10, the front surface window signal processor 220 recognizes a front surface window based on continuous three-dimensional frame data of the front laser scanner 114, measures a distance to the front surface window and reflectivity of the front surface window based on maximum reception intensity in three-dimensional frame data, and transfers a measurement time, distance, and reflectivity to the measurement controller 270.

The rear surface window signal processor 230 recognizes a rear surface window based on continuous three-dimensional frame data of the rear laser scanner 116, measures a distance to a rear surface window and reflectivity of the rear surface window based on maximum reception intensity in three-dimensional frame data, and transfers a measurement time, distance, and reflectivity to the measurement controller 270.

The left side window signal processor 240 recognizes a left side surface window based on continuous three-dimensional frame data of the laser scanner 122, measures a distance to the left side surface window and reflectivity of the left side surface window based on maximum reception intensity in three-dimensional frame data, and transfers a measurement time, distance, and reflectivity to the measurement controller 270.

The right side window signal processor 250 recognizes a right side surface window based on continuous three-dimensional frame data of the laser scanner 132, measures a distance to the right side surface window and reflectivity of the right side surface window based on maximum reception intensity in three-dimensional frame data, and transfers a measurement time, distance, and reflectivity to the measurement controller 270.

The measurement controller 270 receives a signal processing result of each window from the front surface window signal processor 220, the rear surface window signal processor 230, the left side window signal processor 240, and the right side window signal processor 250 (S1010). The signal processing result may include a measurement time, distance, and reflectivity. The measurement controller 270 receives information of a vehicle that is recognized by the vehicle recognition unit 210. Further, the measurement controller 270 receives weather state information from the detection sensor signal processor 260.

The measurement controller 270 calculates a loss coefficient of signal intensity of a laser beam according to a reciprocating distance of a laser beam based on distance data of a signal processing result of each window and a weather state that is received from the detection sensor signal processor 260 (S1020). A loss of signal intensity of a laser beam in the atmosphere generally occurs by scattering and absorption by particles in the atmosphere, and a loss coefficient may be calculated according to a weather state and a characteristic of a laser beam.

The measurement controller 270 corrects reflectivity of each window by reflecting a loss coefficient to reflectivity of a signal processing result of each window, and thus determines reflectivity of each window (S1030). The measurement controller 270 stores reflectivity of each window on a vehicle number basis from information of a vehicle that is recognized by the vehicle recognition unit 210.

The measurement controller 270 estimates transmittance of each window using reflectivity of each window that is stored on a vehicle number basis (S1040). A transmittance of each window may be estimated using a predetermined loss coefficient of a window based on reflectivity of each window and visible ray loss rate information of each window, as in Equation 4.

$$T(w)=1-R(w)-C(w) \qquad \text{(Equation 4)}$$

In Equation 4, T(w) represents transmittance of a window, C(w) represents a predetermined loss coefficient of a window based on visible ray loss rate information of a window, and R(w) represents reflectivity of a window.

The measurement controller 270 stores transmittance of each window on a vehicle number basis.

Thereafter, the measurement controller 270 determines illegality of a window transmittance based on transmittance of each window on a vehicle number basis (S1050). The measurement controller 270 distinguishes an illegal vehicle that deviates from a transmittance reference of the Traffic Tax Act, and stores information of the distinguished illegal vehicle and transmittance information.

Further, the measurement controller 270 provides transmittance of each window on a vehicle number basis and information and transmittance of an illegal vehicle to the online information service unit 300.

Figure 11:
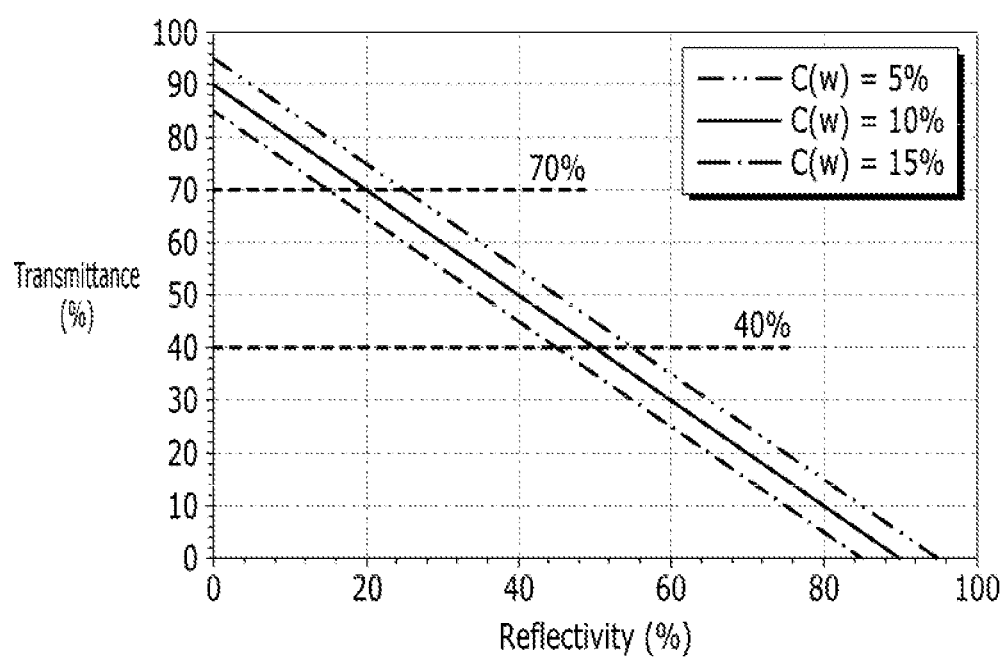
FIG. 11 is a diagram illustrating a relationship of reflectivity and transmittance to a loss coefficient of a window.

FIG. 11 is a diagram illustrating a relationship of reflectivity and transmittance to a loss coefficient of a window.

As shown in FIG. 11, when a loss coefficient range of a window is 5%, 10%, and 15%, reflectivity and transmittance are differently represented. In a vehicle, various kinds of windows may be used on an automaker basis. Therefore, it may be difficult to determine a loss coefficient of a window with a single value. Therefore, a minimum value of a loss coefficient or an intermediate value of a loss coefficient may be applied to a loss coefficient of Equation 4 based on loss coefficients that are investigated for various windows.

At least a partial function of a system and method for remotely sensing visible ray transmittance of a vehicle window according to the foregoing exemplary embodiment of the present invention may be implemented with hardware or may be implemented with software that is combined with hardware.

Figure 12:
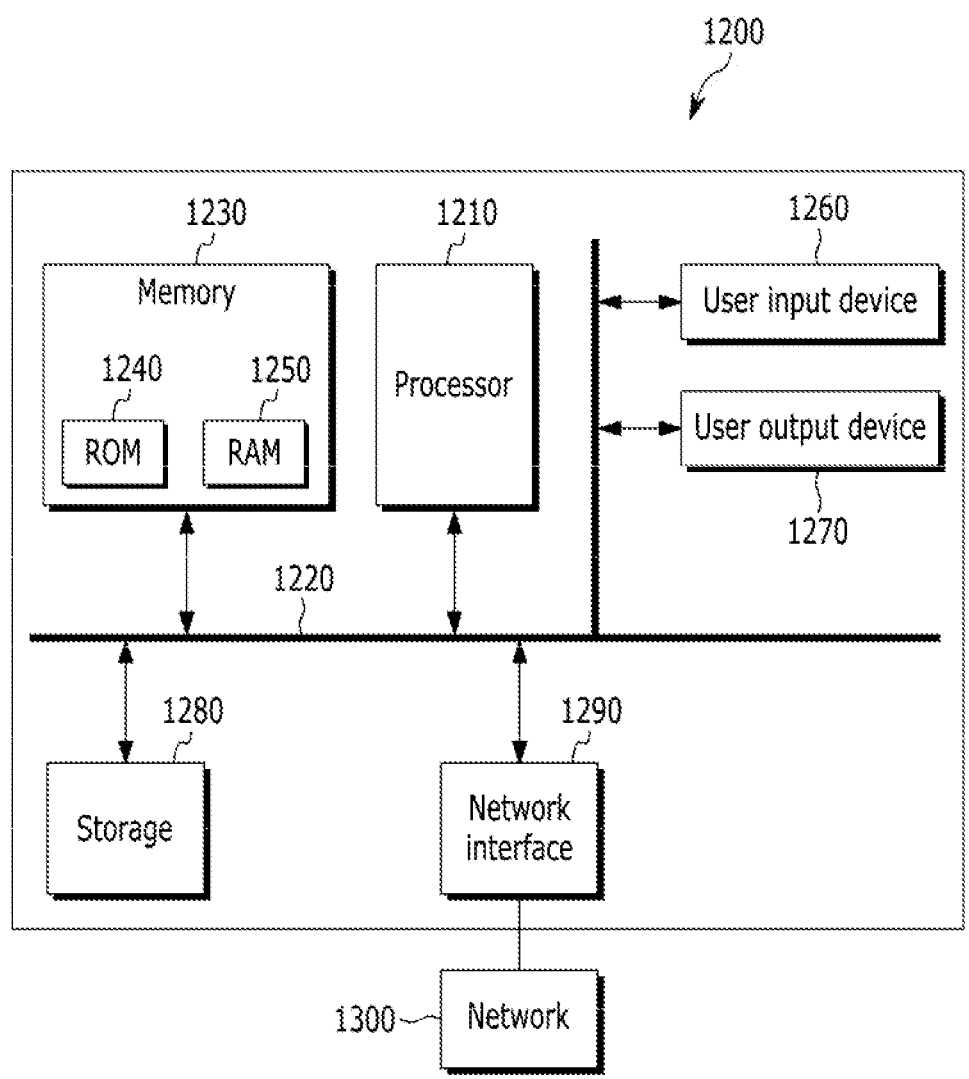
FIG. 12 is a diagram illustrating a vehicle window visible ray transmittance remote sensing system according to another exemplary embodiment of the present invention.

For example, an exemplary embodiment of the present invention may be implemented in a computer system, e.g., as a computer readable medium. FIG. 12 is a diagram illustrating a vehicle window visible ray transmittance remote sensing system according to another exemplary embodiment of the present invention.

As shown in FIG. 12, a computer system 1200 may include one or more of a processor 1210, a memory 1230, a user input device 1260, a user output device 1270, and a storage 1280, each of which communicates through a bus 1220. The computer system 1210 may also include a network interface 1290 that is coupled to a network 1300. The processor 1210 may be a central processing unit (CPU) or a semiconductor device that executes processing instructions stored in the memory 1230 and/or the storage 1280. The memory 1230 and the storage 1280 may include various forms of volatile or non-volatile storage media. For example, the memory may include a read-only memory (ROM) 1240 and a random access memory (RAM) 1250.

The processor 1210 may perform a function of the sensor unit 100, the signal processing controller 200, and the online information service unit 300 of the vehicle window visible ray transmittance remote sensing system.

Accordingly, an embodiment of the invention may be implemented as a computer implemented method or as a non-transitory computer readable medium with computer executable instructions stored thereon. In an embodiment, when executed by the processor, the computer readable instructions may perform a method according to at least one aspect of the invention.

According to an exemplary embodiment of the present invention, by installing a vehicle window visible ray transmittance remote sensing system in an expressway, toll gate, or a facility that is installed at a specific point of a road, a next generation traffic system such as an intelligent traffic system can be effectively implemented. Particularly, the vehicle window visible ray transmittance remote sensing system can remotely sense, analyze, and store information on vehicles that violate or have a high possibility of violating a visible ray transmittance regulation of a vehicle window of the Road Traffic Act and can support an online information service, and thus only vehicles having high illegality can be selected and traffic enforcement and enhancement treatment service can be provided to the vehicles. Resultantly, safer and more effective law regulation of a vehicle window visible ray transmittance that is determined based on the Road Traffic Act can be performed.

An exemplary embodiment of the present invention may not only be embodied through the above-described apparatus and method, but may also be embodied through a program that executes a function corresponding to a configuration of the exemplary embodiment of the present invention or through a recording medium on which the program is recorded, and can be easily embodied by a person of ordinary skill in the art from a description of the foregoing exemplary embodiment.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:
1. A system, comprising:
 a laser scanner that emits a laser beam and that acquires a plurality of pieces of point data of a plurality of points when the laser beam is transmitted through an atmosphere and is reflected from a surface of a vehicle;

an environment sensor unit that detects environment information based on absorption and scattering of laser light in the atmosphere; and a signal processing controller that measures a reflectivity of a window of the vehicle and a distance to the vehicle based on the plurality of pieces of point data, that calculates an external loss coefficient based on the environment information and the distance to the window, that corrects the reflectivity of the window based on the external loss coefficient, and that calculates a transmittance of the window based on the corrected reflectivity of the window and on a predetermined internal loss coefficient of the widow.

2. The system of claim 1, wherein the signal processing controller distinguishes the vehicle when the transmittance of the window deviates from a transmittance reference.

3. The system of claim 1, further comprising a vehicle recognition unit that recognizes identification information of the vehicle, wherein the signal processing controller stores the reflectivity of the window and the transmittance of the window to correspond to identification information of the vehicle.

4. The system of claim 3, further comprising an online information service unit that provides an online service based on the reflectivity of the window and the transmittance that are stored to correspond to the identification information of the vehicle.

5. The system of claim 1, wherein the laser scanner is installed in a facility that is installed on a road.

6. The system of claim 1, wherein the environment sensor unit comprises at least one detection sensor that detects at least one of temperature, humidity, rain, atmospheric pressure, and fine dust.

7. The system of claim 1, wherein the signal processing controller operates the system in a dormant state and a non-dormant state based on the environment information.

8. The system of claim 1, wherein the laser scanner comprises one of:

a front laser scanner that acquires point data of a front window of the vehicle;

a rear laser scanner that acquires point data of a rear window of the vehicle;

at least one left side laser scanner that acquires point data of a left side window of the vehicle; and at least one right side laser scanner that acquires point data of a right side window of the vehicle.

9. The system of claim 8, wherein the at least one of left side laser scanners is installed at different heights, and the at least one right side laser scanner is installed at different heights.

10. The system of claim 1, wherein the plurality of laser scanners use red, green, and blue wavelength regions.

11. The system of claim 1, wherein the signal processing controller determines a transmittance of the window based on a predetermined loss coefficient of the window based on the reflectivity of the window and visible ray loss rate information of the window.

12. The system of claim 1, wherein the signal processing controller measures the reflectivity of the window using point data of a point at which signal intensity of a laser beam is a maximum among the plurality of point data.

13. A method, comprising:
emitting a plurality of laser beams;
acquiring a plurality of point data of a plurality of points in which the plurality of laser beams are transmitted through an atmosphere and are reflected from a surface of a vehicle;
estimating a reflectivity of a window of the vehicle and a distance to the window based on the plurality of point data;
detecting environment information based on absorption and scattering of laser light transmitted by the atmosphere;
calculating an external loss coefficient of the window according to the environment information and the distance to the window;
correcting the estimated reflectivity of the window based on the external loss coefficient;
calculating a transmittance of the window based on the corrected estimated reflectivity and a predetermined internal loss coefficient of the window; and
distinguishing the vehicle when the transmittance of the window deviates from a transmittance reference.

14. The method of claim 13, further comprising:
recognizing identification information of the vehicle;
storing the reflectivity and the transmittance of the window that are measured from the vehicle to correspond to identification information of the vehicle; and
providing an online service based on the reflectivity and the transmittance of the vehicle that are stored to correspond to identification information of the vehicle.

15. The method of claim 13, wherein the estimating of the reflectivity comprises:
measuring the reflectivity of the window and the distance to the window using point data of a point at which signal intensity of a corresponding laser beam is a maximum among the plurality of point data.

16. The method of claim 13, further comprising:
determining an atmosphere state based on the environment information; and
controlling a vehicle window visible ray transmittance remote sensing system in a dormant state and a non-dormant state based on the atmosphere state.

17. The method of claim 13, wherein the emitting of a plurality of laser beams comprises one of:
emitting a plurality of laser beams from a front laser scanner to a front window of the vehicle;
emitting a plurality of laser beams from a rear laser scanner to a rear window of the vehicle;
emitting a plurality of laser beams from a left side laser scanner to a left side window of the vehicle; and
emitting a plurality of laser beams from a right side laser scanner to a right side window of the vehicle.

18. The system of claim 1, wherein the signal processing control estimates the reflectivity of the window and the distance to the window based on a piece of point data having the maximum signal intensity among the plurality of pieces of point data.

19. A system, comprising:
a plurality of laser scanners that emit a plurality of laser beams and that acquire a plurality of pieces of point data of a plurality of points when the plurality of laser beams are reflected from a surface of a vehicle; and
a signal processing controller that measures a reflectivity of a window of the vehicle based on the plurality of pieces of point data and that estimates the reflectivity of the window based on the measured reflectivity of the window, wherein the plurality of laser scanners comprises:
  a front laser scanner that acquires point data of a front window of the vehicle;
  a rear laser scanner that acquires point data of a rear window of the vehicle;
  at least one left side laser scanner that acquires point data of a left side window of the vehicle; and
  at least one right side laser scanner that acquires point data of a right side window of the vehicle.

* * * * *